(12) United States Patent
Michaels

(10) Patent No.: US 6,442,338 B1
(45) Date of Patent: Aug. 27, 2002

(54) ELECTRICAL FUMIGATION DEVICE

(75) Inventor: Kenneth W. Michaels, Spring Grove, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/919,056

(22) Filed: Jul. 31, 2001

(51) Int. Cl.[7] ............................... F24F 3/14; F24F 6/00; A01M 13/00
(52) U.S. Cl. ......................... 392/392; 392/390; 43/125
(58) Field of Search ................................ 392/386, 390, 392/392, 403, 404, 405, 406, 373, 334; 43/125, 129, 130; 239/135, 136

(56) References Cited

U.S. PATENT DOCUMENTS

| | | | | |
|---|---|---|---|---|
| 2,369,623 A | * | 2/1945 | Utley et al. ................... 122/492 |
| 2,541,637 A | | 2/1951 | Christopher et al. | |
| 2,685,020 A | | 7/1954 | Laibow | |
| 2,810,167 A | * | 10/1957 | Parks ........................ 392/324 |
| 2,942,090 A | | 6/1960 | Diehl | |
| 3,152,240 A | * | 10/1964 | Scott ...................... 128/203.27 |
| 3,446,936 A | * | 5/1969 | Hanson et al. ............... 118/726 |
| 3,654,780 A | * | 4/1972 | Frank ......................... 392/404 |
| 4,163,038 A | * | 7/1979 | Nishimura et al. .......... 392/390 |
| 4,810,854 A | * | 3/1989 | Jursich et al. ............... 392/405 |
| 5,402,517 A | * | 3/1995 | Gillett et al. ......... 261/DIG. 89 |
| 5,429,271 A | * | 7/1995 | Porter ...................... 222/146.5 |
| 5,796,914 A | * | 8/1998 | Gatzemeyer et al. ........ 392/390 |

* cited by examiner

Primary Examiner—Sang Paik

(57) ABSTRACT

A fumigation device is provided that is configured to be plugged into an electrical receptacle regardless of its orientation. A housing has an axially extending member with an outer end that is connected to a radially extending member. The radially extending member, in turn, has an outer end defining a delivery port that directs gaseous fumigant away from the wall. A canister is disposed within the housing and defines a cavity having a mouth in communication with the delivery port, the cavity containing a heat-activatable fumigant. A heater supplies heat to the canister when an electrical plug is inserted into the receptacle to activate the active chemical ingredient. A gel trap is disposed downstream of the canister and receives gelled fumigant that might escape from the canister while permitting gaseous fumigant to flow from the canister to the delivery port.

9 Claims, 2 Drawing Sheets

ELECTRICAL FUMIGATION DEVICE

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to wall mountable electrically activated fumigation devices. It appears to be especially well suited for use in permitting such devices to be compatible with electric sockets having varied alignments relative to the wall.

Devices are known for fumigating an enclosed area, such as a room in a house, by expelling a fumigant (e.g. typically an insecticide or fragrance) upon an application of heat. As disclosed in U.S. Pat. No. 5,796,914, some of these devices include a disposable canister containing the fumigant and an electric heater positioned under the fumigant. When activated, these devices produces a fog that is expelled out to fumigate a room or the like.

Before the application of heat, the fumigant is typically in a solid form. It subsequently transforms into a viscous gel material in response to the initial introduction of heat. As a result, it is desirable to direct the mouths of such devices at least partially upwardly to prevent the gel from spilling. While further heating will produce the fog, during the gel phase, there is a spilling potential.

On a vertical wall, blade sockets can be side-by-side, or alternatively one over the other. One previous fumigation device includes a canister/housing assembly whose orientation is fixed with respect to the electrical plug. As a result, the mouth of the canister faces vertically upwardly when the plug is inserted in side-by-side blade holes, but horizontally when the blade holes are one on top of the other. When in this horizontal orientation, gelled fumigant might spill from the fumigation device. Accordingly, the system is not compatible with the latter type of blade hole configuration.

U.S. Pat. No. 5,796,914 provided an improved device having a plug mounted on an angle with respect to the housing, thus allowing the mouth to be positioned at least somewhat upwardly (regardless of the orientation of the electrical receptacle). One potential disadvantage of this device is that the gaseous fumigant is expelled parallel to the direction of extension of the wall. Accordingly, when mounted on a vertical wall, the fumigant will not be directed towards the interior of the room.

A need thus exists for a fumigation device that is compatible with electrical receptacles of varying orientations while directing activated fumigant outwardly towards the interior of the room to be fumigated.

BRIEF SUMMARY OF THE INVENTION

In one aspect the invention provides a fumigation device. There is a housing having an axially extending upstream portion and a transversely extending downstream portion. Preferably the transverse direction is completely radial. However, it might also be somewhat angled.

The downstream portion has an outer end defining a delivery port. There is a chamber disposed within the upstream portion which has a mouth in communication with the delivery port. The chamber contains a heat-activatable fumigant.

There is also an electrical plug extending outwardly from the housing and configured to be received by an electrical receptacle. A heating device is disposed in the housing in electrical communication with the electrical plug and in thermal communication with the chamber.

A trap is configured and positioned to trap non-gaseous flowable fumigant if such non-gaseous flowable fumigant were to escape from the chamber if the upstream portion is horizontally disposed, while permitting gaseous fumigant to flow from the chamber to the delivery port if the upstream portion is horizontally disposed and the heating device is heating the fumigant an electric fumigation device.

In preferred forms the trap has two walls spaced from each other to define a trap pocket there between, each trap wall having an opening there through. The openings are preferably not aligned with each other and the trap walls are connected at their ends with one wall flat and the other dome shaped, or otherwise geometrically receptive to fumigant in liquid form.

The electrical plug can extend from the housing in a first radial direction, and the delivery port can extend from the housing in a second radial direction essentially opposite the first radial direction. In one aspect, when the device is plugged into an electrical receptacle on a flat room wall the upstream portion extends essentially parallel to the room wall. If desired the trap can sit in an outwardly extending flange of the chamber.

In another aspect the invention provides a method of fumigating an area in which an electrical receptacle is mounted on a wall with a fumigating active ingredient. One plugs the above fumigating device into the electrical receptacle, and allows electricity from the electrical receptacle to cause a release of the active ingredient.

The present invention thus achieves mounting flexibility by allowing the fumigator to be vertically or horizontally disposed, without risking gel spillage during heating. Further, fumes are directed away from the wall, thereby avoiding contact with possibly sensitive wall surfaces.

The foregoing and other advantages of the invention will appear from the following description. In the description, reference is made to the accompanying drawings which form a part thereof, and in which there is shown by way of illustration, and not limitation, a preferred embodiment of the invention. Such embodiment does not necessarily represent the full scope of the invention. Reference must therefore be made to the claims herein for interpreting the scope of the invention.

DETAILED DESCRIPTION OF THE PREFERRED EMBODIMENT

Figure 1:
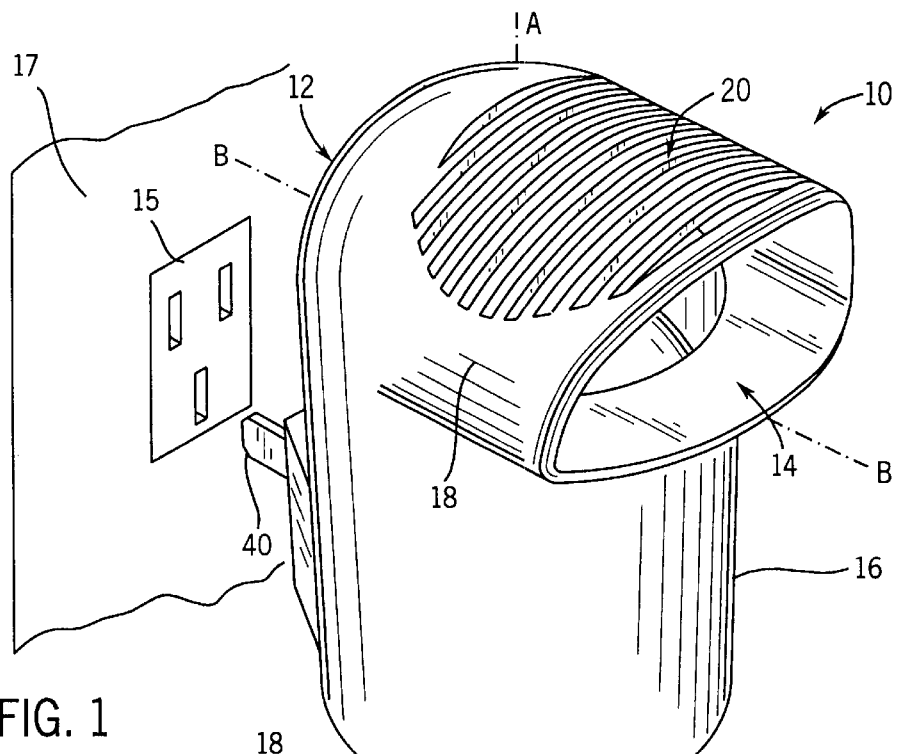
FIG. 1 is a perspective view of a preferred electrical fumigation device of the present invention.

Referring initially to FIG. 1, an electrically activated fumigation device 10 includes a housing 12 defining an enclosure. The housing has a delivery port in the form of opening 14. The delivery port 14 allows activated fumigant to escape from device 10 and into the ambient environment that is to be fumigated.

Housing 12 is preferably unitarily molded of heat-resistant plastic or ceramic material, and includes an annular upstream portion 16 that extends along axis A—A, and a downstream portion 18 extending essentially radially along axis B—B. Portion 18 can be integrally formed with portion 16. The interior of portions 16 and 18, in combination with delivery port 14, define a pathway through which gaseous fumigant travels when being expelled from device 10. The term "downstream" is thus used herein with respect to the direction of travel of gaseous fumigant through the device.

Device 10 is positioned to be plugged into an electrical receptacle 15 having (in the example shown) side-by-side-blade holes. Receptacle 15 is disposed on a flat mounting surface, such as a wall 17.

The device 10 includes a two prong electrical plug 40 that is configured to be plugged in to the receptacle 15. When the device 10 is positioned with respect to the receptacle 15 as illustrated, housing portion 16 extends vertically, and portion 18 is disposed above portion 16 and preferably (albeit not necessarily) extends essentially perpendicularly outwardly from wall 17. Delivery port 14 is formed in the outer end of portion 18.

Accordingly, the fumigant that is expelled through delivery port 14 is directed away from the wall 17 and towards the center of the room to be fumigated. If the receptacle were to have an orientation of one blade hole above the other, device 10 would then be mounted with portion 16 extending horizontally.

Figure 2:
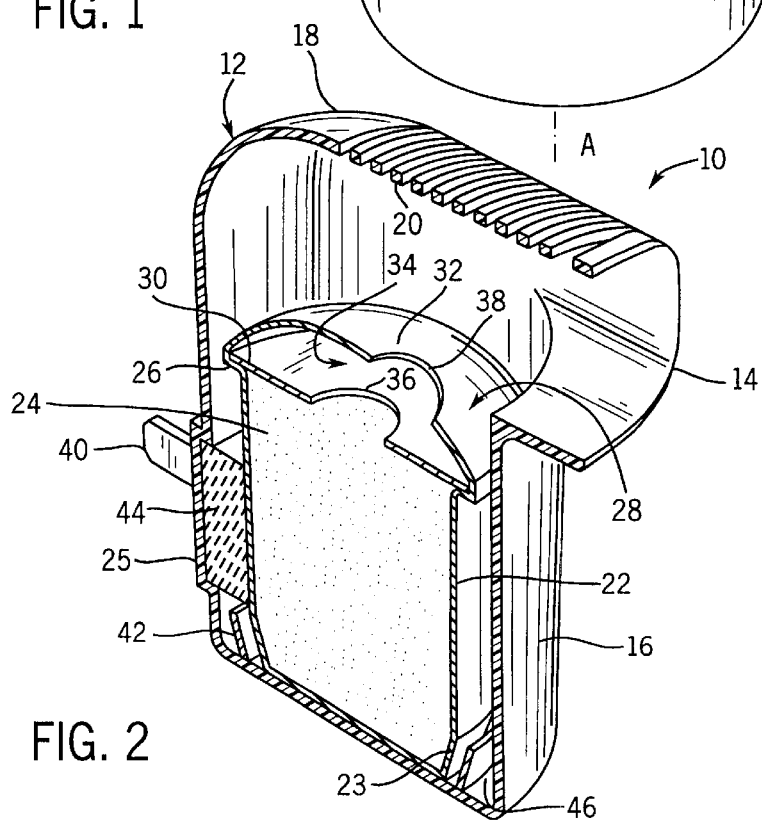
FIG. 2 is a perspective sectional view of the interior of the fumigation device of FIG. 1.
Figure 3:
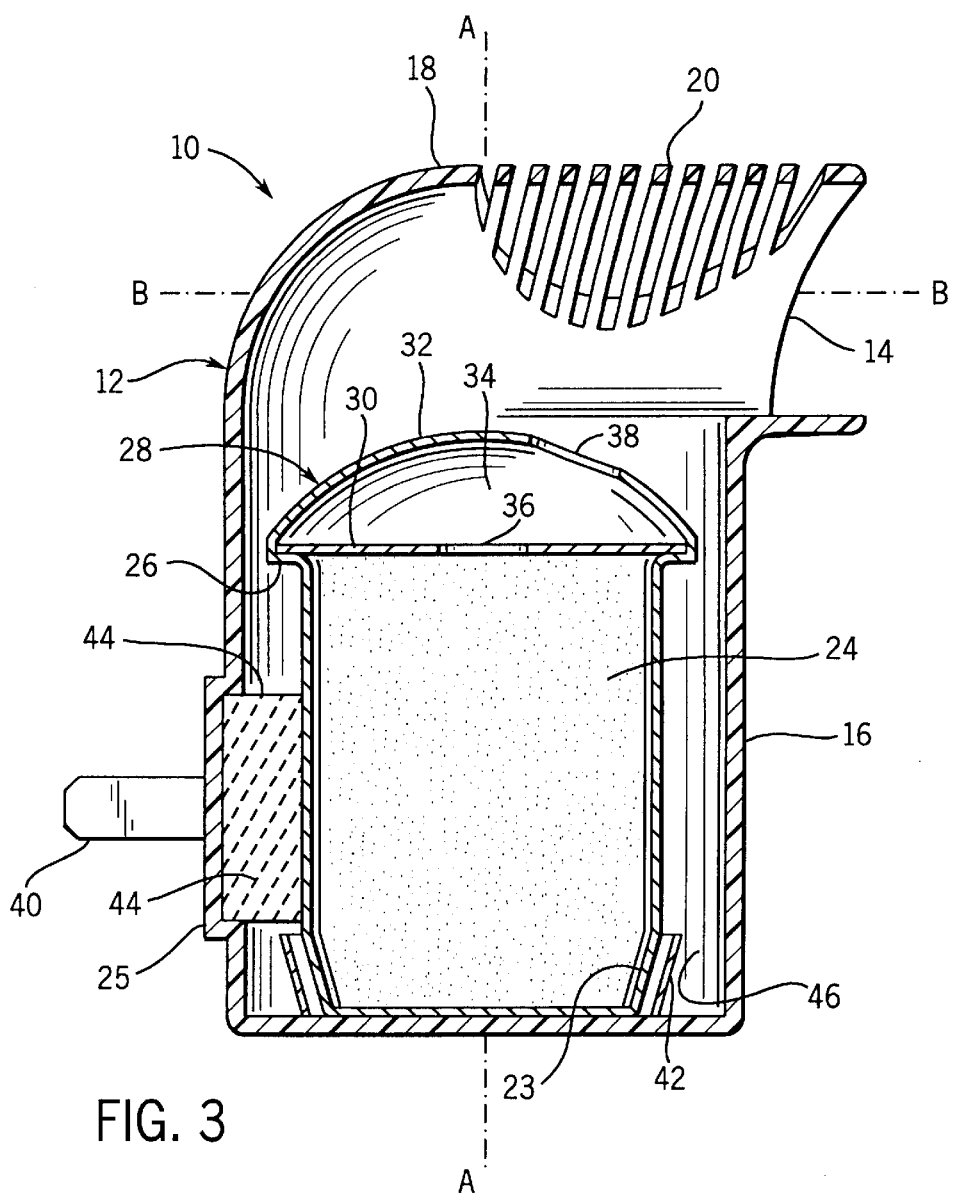
FIG. 3 is a sectional side elevation view of the fumigation device of FIG. 1.

Referring now also to FIGS. 2 and 3, a canister/chamber 22 (which may integrally formed within housing 12, or preferably separately formed therefrom) is disposed within housing 12. Canister 22 is an annular member having a base 23 that is connected to portion 16 either via an adhesive or mechanical fastener, or the like. Canister 22 extends axially and is centrally disposed in the portion 16 with respect to axis A—A.

Because canister 22 may not be removed from the housing 12 without the effective destruction of the fumigation device 10, it is assured that the fumigation device can only be used once. Canister 22 defines an open volume containing a heat-activatable chemical charge 24. The chemical charge 24 preferably includes an active fumigation ingredient and blowing agent for expelling activated fumigant from the canister 22 by a self-sustaining chemical reaction. The blowing agent may combust or, preferably, be a heat-activatable but non-combusting blowing agent, such as azodicarbonamide.

The fumigant is preferably an insecticide such as permethrin mixed with azodicarbonamide, starch and a fragrance. However, a wide variety of other synthetic and naturally occurring insecticides would also work. In addition, antibacterial and air freshening products may be used, as may other blowing agents. The preferred form of the pellets is cylindrical, but granulated or spherical forms are also possible. When chemical charge 24 is exposed to heat source 42 the fumigant transforms from a solid to a gel, and eventually to a gas that is expelled from the device 10 by the blowing agent.

Canister 22 includes, at its axially outer end, an annular flange 26 extending therefrom that provides a seat for a gel trap 28. In particular, trap 28 includes a flat annular base plate 30 that rests directly on flange 26, and a dome-shaped outer wall 32 connected to plate 30 at its outer end. Walls 30 and 32 thus define a void 34 there between that is sized to receive gelled if chemical charge 24 that spills from the canister 22.

Base plate 30 defines a bore 36 that is preferably centrally disposed about axis A—A, and that extends axially from the void 34 and into the open volume of canister 22 containing the chemical charge 24. Surface 32 defines a bore 38 extending from the void and towards delivery port 14. In particular, bore 38 is radially offset from axis A—A and extends radially outwardly towards delivery port 14.

When heat is applied from heat source 42 to the canister 22, the fumigant transitions from a solid state, to a gel, and ultimately to a gas that is expelled from the device. If receptacle 15 is in a "one above the other" orientation such that portion 16 and canister 22 extend horizontally, the gel will be retained within the enclosure of trap 28 should it leak out of the chamber before it turns to gas, thus preventing the gel from escaping out the fumigation device 10. Nevertheless, gaseous fumigant may travel from canister 22, through bores 36 and 38, and out the delivery port 14.

As a further measure for preventing spillage of gelled fumigant from the device, a wire mesh or screen (not shown) could be mounted onto or fabricated directly into either or both surfaces 30 and 32 to cover corresponding bores 36 and 38, at least with respect to preventing solid pellets from falling out.

As discussed above, the fumigation device 10 includes an electrical connector in the form of a plug 40 that is fixedly mounted onto portion 16 and extends radially outwardly in a direction parallel delivery port 14. The electrical plug 40 is configured to be plugged into electrical receptacle 15, regardless of its orientation while avoiding the complexities associated with rotating parts on the fumigation device 10.

While plug 40 is illustrated having a side-by-side orientation when portion 16 extends vertically, it should be easily appreciated that the device may be constructed such that the plug 40 is mounted onto housing 12 in alternative orientations. For example, the plug 40 may be vertically disposed when the portion 16 extends vertically. Alternatively still, plug 40 could have an angular orientation with respect to portion 16, in which case the canister 22 would extend at least partially upwardly regardless of the orientation of the electrical receptacle.

Regardless of the orientation of the receptacle 15 and plug 40, portion 16 extends substantially parallel to wall 17, and portion 18 preferably extends substantially perpendicularly or slightly angled away from wall and into the environment to be fumigated.

An axially extending annular heating device in the form of an electrical band heater 42 circumscribes the base 23 of canister 22. Electrical block 44 is seated in a recess 25 in the housing 12. Electrical block 44 contains standard circuitry that electrically connects the electrical plug 40 to heater 42.

Accordingly, when the plug 40 is inserted into electrical receptacle 15, power is received by heater 42 which, in turn, delivers heat to the outer periphery of the canister 22. A preferred heater is of the PTC or wire wound type. Because a substantial surface of canister 22 is in thermal communication with the heating element 42, the chemical charge 24 is heated substantially uniformly.

Canister 22 is preferably a seamless, metallic can suitable for conducting heat. In particular, if heater 42 is a low wattage heater, the canister is then preferably made of iron. Alternatively, if the heater 42 is more powerful, it will be desirable to implement an aluminum canister.

During operation of the fumigation device 10, heat is generated both from operation of the heating device 42 as well as the reaction of the blowing agent in the chemical charge 24. As a result, the housing 12 must be capable of withstanding that heat and retaining its structural integrity. In order to reduce the amount and intensity of the heat that is experienced by the housing 12, the canister 22 is disposed inwardly with respect to the housing to define an insulating air gap 46 that is disposed therebetween. Furthermore, a vent 20 comprising a plurality of laterally extending grooves disposed in the axially outer wall of member 18, allows the heated air in the housing 12 to be replaced by cooler air from the ambient environment. Vents 20 are preferably directionally louvered to add in the dispersal of the fumigant gases away from the wall.

Preferably, the heating device 42 is non-renewably self-disabling after heating sufficiently to initiate the action of the blowing agent. Accordingly, use of the fumigation device 10 subsequent to the activation of the blowing agent is prevented. In particular, the heating device 42 is preferably destroyed non-renewably upon its first use, thereby again requiring that the fumigation device 10 be a single use device.

The invention has been described in connection with what is presently considered to be the most practical and preferred embodiment. However, the present invention has been presented by way of illustration and is not intended to be limited to the disclosed embodiment. Accordingly, those skilled in the art will realize that the invention is intended to encompass all modifications and alternative arrangements included within the spirit and scope of the invention, as set forth by the appended claims

INDUSTRIAL APPLICABILITY

The present invention provides an electric fumigator that minimizes fumigant spillage and is operable regardless of the orientation of the electrical receptacle.

I claim:

1. A fumigation device, comprising:
    a housing having an axially extending upstream portion and a transversely extending downstream portion, wherein the downstream portion has an outer end defining a delivery port;
    a chamber disposed within the upstream portion and having a mouth in communication with the delivery port, the chamber containing a solid heat-activatable fumigant;
    an electrical plug extending outwardly from the housing and configured to be received by an electrical receptacle alternatively in a horizontal or vertical orientation;
    a heating device disposed in the housing in electrical communication with the electrical plug and in thermal communication with the chamber; and
    a trap in the form of a pocket suitable to trap non-gaseous flowable fumigant while also permitting gaseous fumigant to flow from the chamber to the delivery port when the upstream portion is not vertically disposed and the heating device is heating the fumigant.

2. The fumigation device as recited in claim 1, wherein the trap further comprises two walls spaced from each other to define a trap pocket there between, each trap wall having an opening there through.

3. The fumigation device as recited in claim 2, wherein an opening in a first said trap wall is essentially centrally located along the first trap wall, and an opening in the second said trap wall is not axially aligned with the opening in the first trap wall.

4. The fumigation device as recited in claim 3, wherein the first and second trap walls are connected at their outer ends.

5. The fumigation device as recited in claim 4, wherein the first trap wall is substantially flat, and wherein the second trap wall is substantially dome shaped.

6. The fumigation device as recited in claim 1, wherein the electrical plug extends from the housing in a first radial direction, and the delivery port extends from the housing in a second radial direction essentially opposite the first radial direction.

7. The fumigation device is recited in claim 1, wherein when the device is plugged into an electrical receptacle on a flat room wall the upstream portion extends essentially parallel to the room wall.

8. The fumigation device as recited in claim 1, wherein the trap sits in an outwardly extending flange of the chamber.

9. A method of dispensing a fumigant comprising the steps of:
    (a) providing a fumigation device comprising:
        (i) a housing having an axially extending upstream portion and a transversely extending downstream portion, wherein the downstream portion has an outer end defining a delivery port;
        (ii) a chamber disposed within the upstream portion and having a mouth in communication with the delivery port, the chamber containing a solid heat-activatable fumigant;
        (iii) an electrical plug extending outwardly from the housing;
        (iv) a heating device disposed in the housing in electrical communication with the electrical plug and in thermal communication with the chamber; and
        (v) a trap defining a pocket disposed adjacent the chamber;
    (b) positioning the fumigation device such that the upstream portion extends essentially horizontally;
    (c) applying power to the heating device to heat the fumigant and allow gaseous fumigant to escape from the fumigation device; and
    (d) trapping gelled fumigant that is produced during step (c) and that flows from the chamber inside the trap.

* * * * *